(12) United States Patent
Forlani et al.

(10) Patent No.: US 10,384,014 B2
(45) Date of Patent: Aug. 20, 2019

(54) SENSING SYSTEM FOR DETECTING A PISTON IN A MEDICAL FLUID CONTAINER

(71) Applicant: Eli Lilly and Company, Indianapolis, IN (US)

(72) Inventors: Christian Fabio Forlani, Milan (IT); Rossano Claudio Massari, Milan (IT); Mehran Mojarrad, Thousand Oaks, CA (US)

(73) Assignee: Eli Lilly and Company, Indianapolis, IN (US)

(*) Notice: Subject to any disclaimer, the term of this patent is extended or adjusted under 35 U.S.C. 154(b) by 101 days.

(21) Appl. No.: 15/505,699

(22) PCT Filed: Aug. 27, 2015

(86) PCT No.: PCT/US2015/047172
§ 371 (c)(1),
(2) Date: Feb. 22, 2017

(87) PCT Pub. No.: WO2016/036574
PCT Pub. Date: Mar. 10, 2016

(65) Prior Publication Data
US 2017/0246399 A1 Aug. 31, 2017

Related U.S. Application Data

(60) Provisional application No. 62/044,486, filed on Sep. 2, 2014.

(51) Int. Cl.
*A61M 5/31* (2006.01)
*A61M 5/315* (2006.01)
(Continued)

(52) U.S. Cl.
CPC ...... *A61M 5/31568* (2013.01); *A61M 5/1684* (2013.01); *A61M 5/20* (2013.01);
(Continued)

(58) Field of Classification Search
CPC .. A61M 2205/3306; A61M 2205/3389; A61M 2205/587; A61M 5/3129; A61M 5/31568
See application file for complete search history.

(56) References Cited

U.S. PATENT DOCUMENTS 5,376,785 A * 12/1994 Chin ............... G01D 5/30
250/214 PR
5,523,560 A 6/1996 Manique et al.
(Continued)

FOREIGN PATENT DOCUMENTS

EP 1920793 11/2006
WO 9408208 4/1994
(Continued)

*Primary Examiner* — William R Carpenter
(74) *Attorney, Agent, or Firm* — Daniel Spillman

(57) ABSTRACT

A sensing system for determining a position of a plunger within a fluid container. The sensing system includes a light source, a light detector and a controller. The light source is configured to emit light into a barrel wall of the fluid container so that the barrel wall serves as a waveguide to guide the light to travel therein in an axial direction. The light detector is positioned to detect reflected light that was emitted by the light source, traveled through the barrel wall serving as the waveguide, and then reflected off a surface of the plunger. The controller is in communication with the light detector to determine an axial position of the plunger surface based on data from the light detector of the detected reflected light.

26 Claims, 11 Drawing Sheets

(51) Int. Cl.
*A61M 5/168* (2006.01)
*A61M 5/20* (2006.01)
*A61M 5/145* (2006.01)

(52) U.S. Cl.
CPC ......... *A61M 5/3129* (2013.01); *A61M 5/1452* (2013.01); *A61M 2005/3126* (2013.01); *A61M 2205/3306* (2013.01); *A61M 2205/3389* (2013.01); *A61M 2205/587* (2013.01)

(56) References Cited

U.S. PATENT DOCUMENTS

| | | | |
|---|---|---|---|
| 5,628,309 | A | 5/1997 | Brown |
| 5,720,733 | A | 2/1998 | Brown |
| 5,782,814 | A | 7/1998 | Brown et al. |
| 5,792,117 | A | 8/1998 | Brown |
| 6,013,020 | A | 1/2000 | Meloul et al. |
| 6,068,615 | A | 5/2000 | Brown et al. |
| 6,110,148 | A | 8/2000 | Brown et al. |
| 6,111,653 | A * | 8/2000 | Bucknell ............... G01N 21/474 356/445 |
| 6,113,578 | A | 9/2000 | Brown |
| 6,385,507 | B1 | 5/2002 | Buijtels |
| RE38,189 | E | 7/2003 | Walker et al. |
| 6,685,678 | B2 | 2/2004 | Evans et al. |
| 7,018,363 | B2 * | 3/2006 | Cowan ................ A61M 5/1452 604/151 |
| 7,074,209 | B2 | 7/2006 | Evans et al. |
| 7,115,113 | B2 | 10/2006 | Evans et al. |
| 7,462,166 | B2 * | 12/2008 | Cowan ............... A61M 5/14546 604/131 |
| 7,682,345 | B2 * | 3/2010 | Savage ................ A61M 5/007 604/228 |
| 8,036,444 | B2 | 10/2011 | Nielsen |
| 8,049,519 | B2 | 11/2011 | Nielsen et al. |
| 8,197,449 | B2 * | 6/2012 | Nielsen ............... A61M 5/3155 604/187 |
| 8,308,698 | B2 | 11/2012 | Wagner et al. |
| 8,817,258 | B2 | 8/2014 | Whalley et al. |
| 2001/0034506 | A1 | 10/2001 | Hirschman et al. |
| 2003/0105430 | A1 | 6/2003 | Lavi et al. |
| 2004/0082918 | A1 | 4/2004 | Evans et al. |
| 2004/0135078 | A1 | 7/2004 | Mandro et al. |
| 2005/0080384 | A1 * | 4/2005 | Green, Jr. ........ A61M 5/31511 604/218 |
| 2008/0243088 | A1 | 10/2008 | Evans |
| 2008/0255525 | A1 | 10/2008 | Taufig |
| 2009/0299279 | A1 | 12/2009 | Richter |
| 2012/0268741 | A1 * | 10/2012 | Pommereau ............ G06F 19/00 356/343 |
| 2015/0085286 | A1 * | 3/2015 | Whalley ................ A61M 5/31 356/434 |
| 2017/0056604 | A1 * | 3/2017 | Cowan ................ A61M 5/365 |

FOREIGN PATENT DOCUMENTS

| | | |
|---|---|---|
| WO | 02056934 | 7/2002 |
| WO | 2007107558 | 9/2007 |
| WO | 2008040479 | 4/2008 |
| WO | 2011032960 | 3/2011 |
| WO | 2013004844 | 1/2013 |
| WO | 2013012526 | 1/2013 |
| WO | 2013050535 | 4/2013 |

* cited by examiner

SENSING SYSTEM FOR DETECTING A PISTON IN A MEDICAL FLUID CONTAINER

BACKGROUND OF THE INVENTION

The present invention pertains to fluid delivery devices, and, in particular, to a sensing system for determining the position of a plunger within a fluid container.

A variety of known types of devices used to deliver fluid medication to a patient utilize medication-filled containers having movable plungers, such containers including cartridges and syringes. These types of devices include, but are not limited to, infusion pumps such as insulin pumps and medication injectors such as injection pens. A medication cartridge includes a movable plunger that seals medication within a barrel of the cartridge forward of the plunger. The cartridge plunger, when advanced by a drive mechanism of the delivery device in which the cartridge may be installed, forces medication from the cartridge through an outlet of that cartridge for delivery to a user.

Knowing the axial position of a plunger within a container allows for various types of information to potentially be available to a user. For instance, the absolute position of the plunger may allow a determination of the quantity of medication remaining in the container. In addition, changes in axial position of the plunger may allow a determination of a dose dispensed from the container.

A variety of systems previously have been developed to determine in some fashion the position of a plunger within a container. One such type of system uses optic properties. U.S. Pat. No. 6,113,578 discloses a number of designs that permit optical dose measurements in syringes. While potentially useful, these designs are not without their shortcomings. For instance, these designs are relatively complex in that they require a significant number of operative components. This complexity can result in greater costs associated with manufacture. Still further, this complexity may increase the number of potential failure modes, as well as require more space than is desired when incorporated in devices that are desired to be kept small, compact and portable.

Thus, it would be desirable to provide a plunger sensing system, or a device that employs such a sensing system, that can overcome one or more of these and other shortcomings of the prior art.

BRIEF SUMMARY OF THE INVENTION

In one form thereof, the present invention provides a sensing system for determining a position of a plunger within a fluid container, the fluid container including a barrel made of a light transmitting material, the barrel extending in an axial direction between a forward outlet end and a rearward end, the plunger having at least one peripheral surface region in fluid tight engagement with an interior surface of a wall of the barrel to seal fluid in the barrel forward of the plunger, and the plunger advanceable in the axial direction within the barrel toward the forward outlet end for dispensing the fluid from the fluid container through the forward outlet end. The sensing system includes a light source, a light detector and a controller. The light source is configured to emit light into the barrel wall so that the barrel wall serves as a waveguide to guide the light to travel therein in the axial direction. The light detector is positioned to detect reflected light that was emitted by the light source, traveled through the barrel wall serving as the waveguide, and then reflected off the at least one peripheral surface region. The controller is in communication with the light detector to determine an axial position of the at least one peripheral surface region within the fluid container based on data from the light detector of the detected reflected light.

In another form thereof, the present invention provides a medication delivery device including a housing including a container retainer, a medication container held within the container retainer, the medication container including a barrel and a plunger, the barrel made of a light transmitting material and extending in an axial direction between a forward outlet end and a rearward end, the plunger having at least one peripheral surface region in fluid tight engagement with an interior surface of a wall of the barrel to seal medication in the barrel forward of the plunger, an advancing mechanism within the housing operable to advance the plunger within the barrel to dispense medication from the medication container through the forward outlet end, a light source mounted within the housing to emit light into the barrel wall so that the barrel wall serves as a waveguide to guide the light to travel therein in the axial direction, a light detector mounted within the container retainer to detect reflected light that was emitted by the light source, traveled through the barrel wall serving as the waveguide, and then reflected off the at least one peripheral surface region, and a controller mounted within the housing in communication with the light detector to determine an axial position of the at least one peripheral surface region within the medication container based on data from the light detector of the detected reflected light.

One advantage of the present invention is that a system for sensing a plunger within a container may be provided which is simple so as to have a relatively low cost to manufacture.

Another advantage of the present invention is that a system for sensing a plunger within a container may be provided which allows for a determination of plunger position and movement within the container.

Still another advantage of the present invention is that a system for sensing a plunger may be provided which allows for compression of the plunger to be determined.

Still another advantage of the present invention is that a system for sensing a plunger within a container may be provided which only requires limited space so as to allow a delivery device in which such is incorporated to remain compact and easy to handle.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
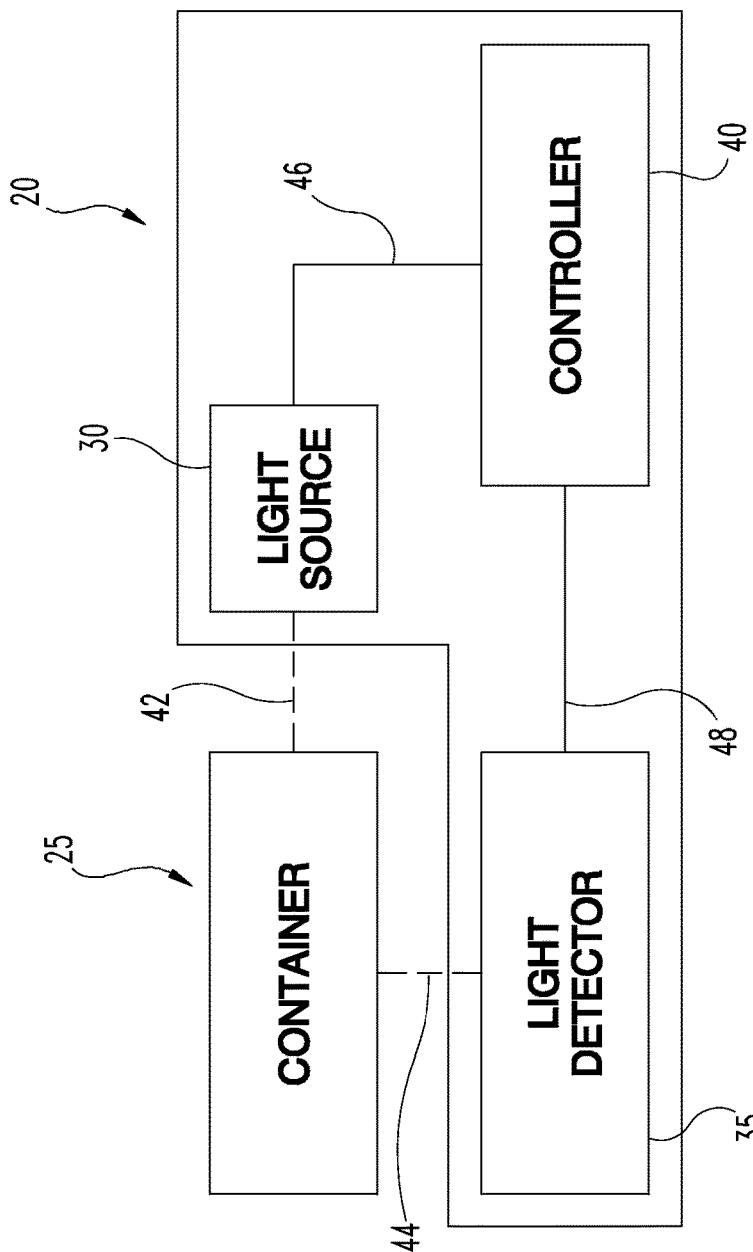
FIG. 1 is schematic illustration of a sensing system of the present invention along with a container with which such system is advantageously utilized.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

In FIG. 1, there is shown schematically a first embodiment of a sensing system of the present invention, generally designated 20, being used with a container generally indicated at 25. Sensing system 20 includes a light source 30, a light detector 35 and a controller 40. Light source 30 is positioned to operatively interact with container 25 by providing a light into the container wall as indicated at dashed line 42. Light detector 35 is positioned to operatively interact with container 25 by detecting light reflected from the container as indicated at dashed line 44. Controller 40 controls the operation of sensing system 20 and may be part of the overall control system of a device in which system 20 may be installed. Controller 40 uses data received from light detector 35 to determine information related to the container, such as the position of the plunger within the container which may be used to calculate fluid within the container, or changes in position of the plunger for determining output from the container, or plunger compression. The block shown as controller 40 in FIG. 1 can also be considered a power source for the elements of the sensing system 20 that require an external power source for operation.

Controller 40 is shown operatively connected at 46 to light source 30, and at 48 to light detector 35. Connections 46 and 48 allow controller 40 to make light source 30 and light detector 35 operational only when necessary for plunger position determinations, thereby conserving energy when such energy is provided by an external source, other than ambient light as described below. Any necessary electrical power can be provided in one or more of a number of suitable ways, such as by fixed or rechargeable batteries, or external power supply, or supercapacitors, or energy harvesting systems such as solar, inductive, forced/free convection gas flow, radio frequency, vibration or kinetic, or thermoelectric. Connection 48 also represents a data line by which output of light detector 35 reaches controller 40 for processing.

Figure 2:
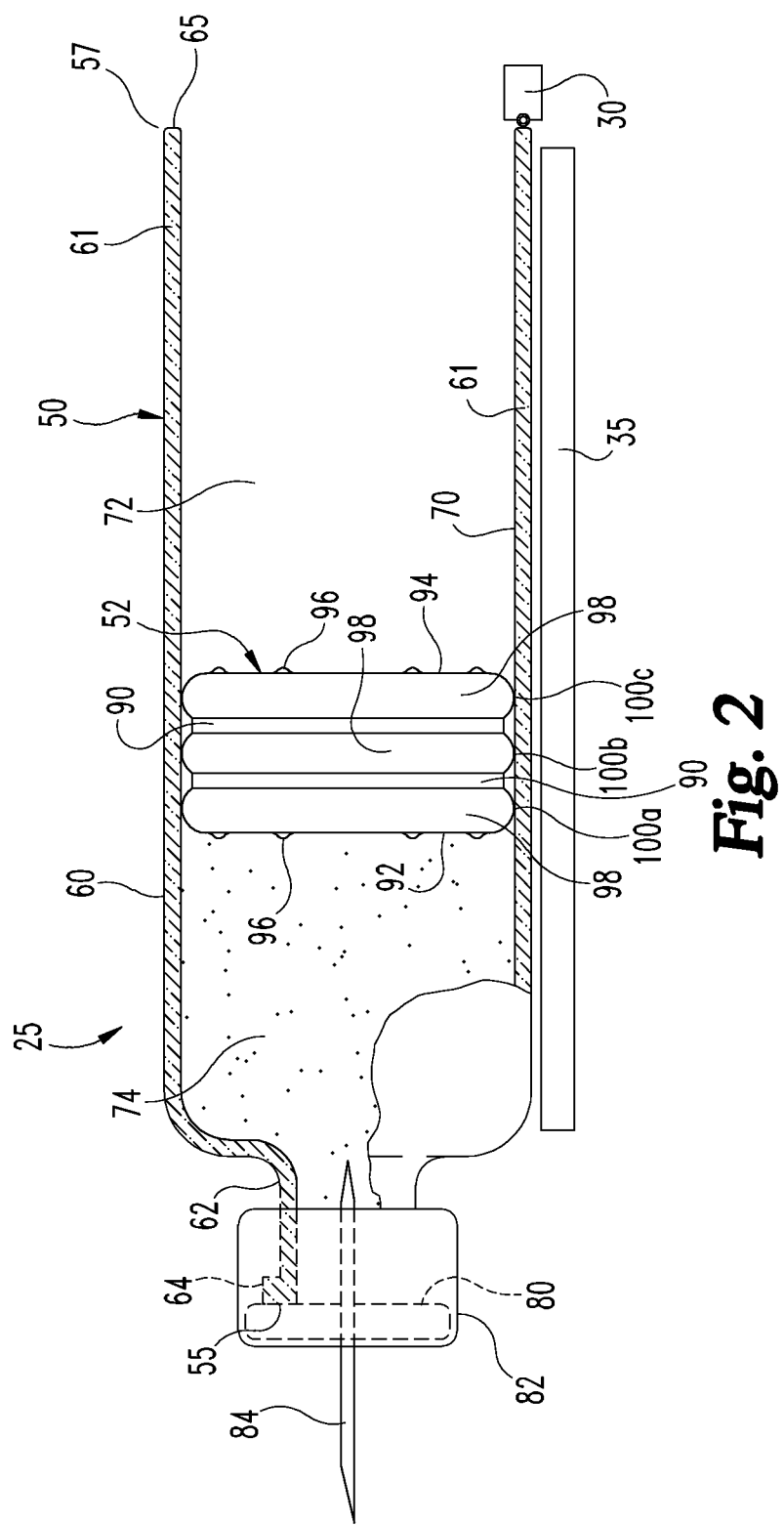
FIG. 2 is a diagrammatic view of select components of the sensing system of FIG. 1 disposed in an operational configuration around a medication cartridge shown in partial cross-sectional side view.

With reference to FIG. 2, light source 30 and light detector 35 are shown abstractly and in operational positions along one form of fluid container 25 with which sensing system 20 finds beneficial application. Sensing system 20 is based on optic properties and is configured to use a wall of container 25 as a waveguide so as to allow for position determinations of one or more portions of the container plunger. Container 25 is shown in FIG. 2 as a standard medication-filled cartridge that can be used in, for example, a medication injection pen. As sensing system 20 can be adapted for detecting plungers in other differently configured containers, for example in conventional syringes having drivable rods that extend from the plungers and which project beyond syringe barrels, the container shown in FIG. 2 and its description herein is to be considered illustrative and not limiting.

Light source 30 provides a visible light that is directed into the container wall in an axial direction so as to cause an illumination of the portions of the cartridge plunger which sealingly contact the cartridge barrel. In alternate embodiments, rather than a visible light, the light wavelength can be elsewhere within the infrared to ultraviolet wavelength range, provided the remainder of the sensing system, and the material of the cartridge, are selected to be suitable therewith.

A suitable light source 30 can be a single light in line with the barrel wall and that directs its light into the container wall at only a small segment of the circumference of the container barrel. A suitable light source 30 could alternatively be provided by multiple lights instead of just one light. The light from light source 30 which moves through the cartridge wall acting as a waveguide is sufficiently intense for the portion of that light that is reflected off the sealing plunger portions to be measured by light detector 35. The intensity of light directed by light source 30 is also greater than that of any otherwise present light incident on any portion of the barrel directly between the light detector 35 and the plunger 52 or any point along the cartridge barrel 50.

A light emitting diode (LED) that provides a narrow light beam is preferred as light source 30. Laser or other light sources, such as florescent or incandescent, are also usable. The light beam may be white or colored light, such as red, blue or green, so long as it is recognizable or detectable by light detector 35. One suitable LED is available from Avago Technologies as HLMP-Q106. A dedicated lens or a group of lenses may be provided to focus the light beam from the light source into the barrel thickness.

Light detector 35 is a sensing element intended to register light reflected from the cartridge 25 at different points along the detector length. In particular, light detector 35 is positioned to sense light beams reflected outside the cartridge after these light beams have traveled within the waveguide provided by the cartridge wall after being generated by the light source 30. Such reflection has been found to be highest in correspondence to the portion or portions of the plunger which are in a fluid sealing engagement with the inner surface of the cartridge wall. Light detector 35 is shown positioned to be in radial alignment with light source 30, though not directly radially outward thereof, relative to the axis of cartridge 25. Such an alignment is not required as the light detector may be effective when angularly spaced from the light source. Light detector 35 converts the reflected light registered to electrical signals that are transmitted via line 48 to controller 40.

In one embodiment, light detector 35 may be a linear array of complimentary metal-oxide semiconductor elements (CMOS) that is sized to axially extend along at least the portion of the cartridge length at which the positions of the cartridge plunger sealing portions are desired to be detected. Light detector 35 may extend the entire axial length of barrel main body section 60. Other types of light detectors could alternatively be used to detect reflected light, such as a linear charge-coupled device array (CCD), photodiodes array, photoresistors array, position-sensitive diodes, and further two-dimensional image sensors could be used.

Figure 8:
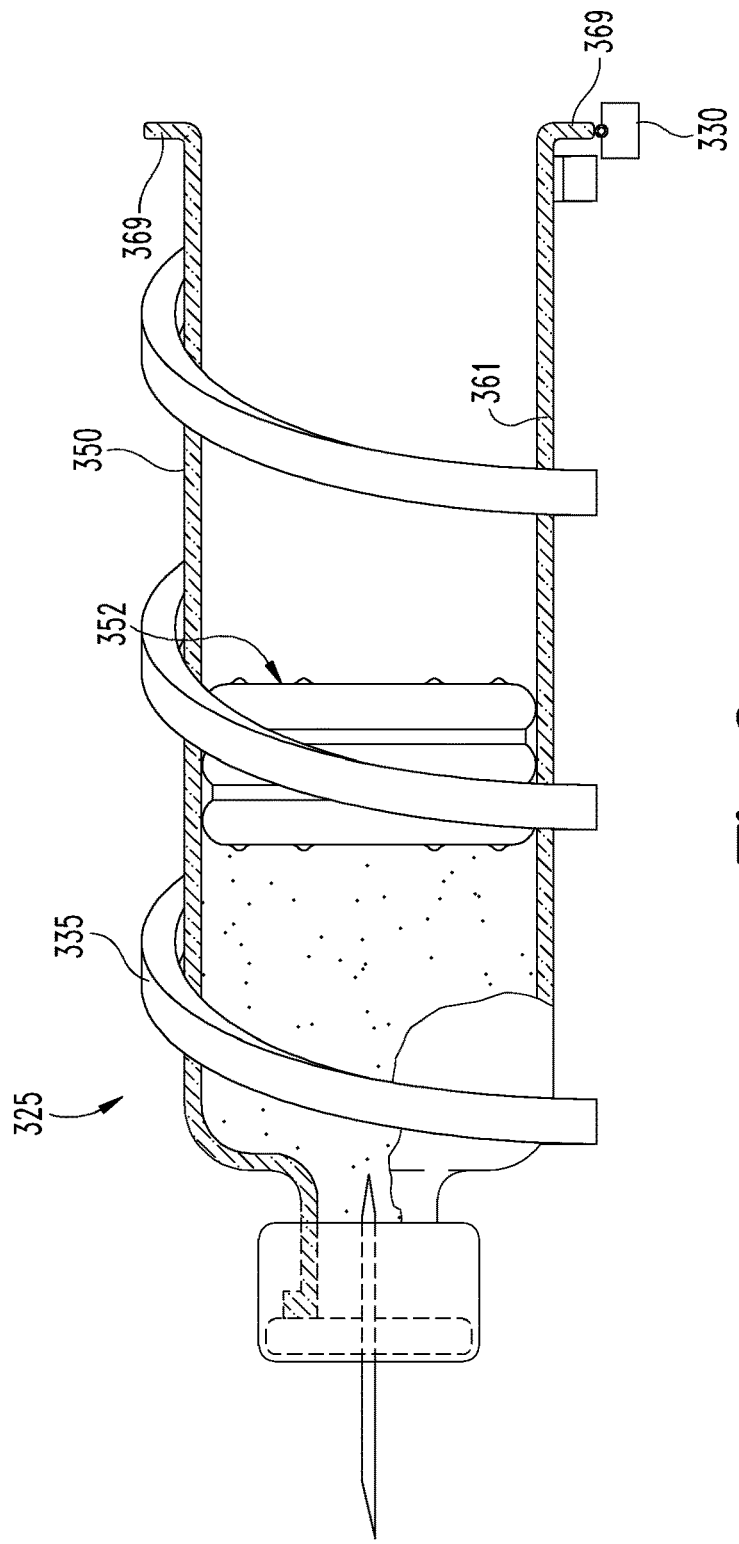
FIG. 8 is diagrammatic view, conceptually similar to FIG. 2, of select components of still another alternate sensing system of the present invention adapted for another differently configured cartridge.

In another embodiment, instead of a straight detector, a CMOS detector may be laid out in a non-linear arrangement around the cartridge main body, such as in a helical pattern as shown in FIG. 8. Such a helical pattern may be used to accommodate for spatial restrictions. In addition, a helical pattern can allow for greater detection resolution as along the axial length of the cartridge the array can include more detector elements.

Cartridge 25 is shown as being a standard 3 milliliter medication cartridge including a barrel 50 and a sealing plunger 52 that is movable along a portion of the axial length of the barrel. Barrel 50 is formed in one piece in a cylindrical tubular form extending in an axial direction between a forward end 55 and a rearward end 57. The references to forward and rearward relate to a directional naming convention in which during dose dispensing the plunger 52 is considered to move forward within the cartridge barrel. The tubular barrel 50 defines an interior hollow 72. Barrel 50 includes a main body section 60, and a stepped down neck section 62 with a septum support collar 64 at a forward end of the neck section.

Barrel main body section 60 is formed by an axially extending, tubular cylindrical wall 61 having an interior surface 70 that the sealing surfaces of plunger 52 engage and slide along in a fluid-tight manner. The portion of interior hollow 72 forward of plunger 52 is filled with medication 74 for dispensing. When the plunger 52 is advanced in the forward axial direction within the barrel, or to the left in FIG. 2, medication is dispensed from container 25 by passing through the outlet of the barrel 50 formed by the open forward end of the hollow 72 at the forward end 55 of barrel 50.

For the shown cartridge 25 intended to be used with a needle, the barrel outlet is capped by a septum 80 secured by a crimp seal 82. A double ended needle abstractly shown at 84 pierces septum 80 to provide a passageway by which medication 74 can pass from the barrel outlet through the septum 80 when plunger 52 is driven forward. Needle 84 is often associated with an injection needle assembly that can be removably mounted to, for example, an injection pen in which cartridge 25 is installed for use.

Barrel 50 is made of a material that transmits within the barrel wall the light applied by light source 30. Transparent or translucent light transmitting glass or polymers are suitable barrel materials. Barrel 50 is shown being of uniform construction around its circumference. This results in sensing system 20 being operative for any angular orientation of the cartridge 25 relative to the axial direction, resulting in cartridge placement with the sensing system 20 being relatively uncomplicated. Sensing system 20 could be used with a cartridge that is not so uniformly constructed so long as the portion of such a cartridge aligned with a light source 30 and light detector 35 is constructed to allow light transmission as described more fully below.

Plunger 52, which is not shown in cross-section in FIG. 2, is designed to have at least one peripheral surface region in fluid tight engagement with barrel interior surface 70 to seal medication 74 from the barrel rearward end 57. Plunger 52 is formed in the shown embodiment from a single piece of resilient or elastomeric material, such as bromobutyl rubber. Plunger 52 includes a body 90 having a forward end 92 and a rearward end 94 that are each oriented transverse to the axial direction in which the length of the plunger body 90 extends. The face of each of forward end 92 and rearward end 94 is flat but for a series of projecting nubs 96 that aid in preventing multiple plungers, during the manufacturing process, from sticking together. The end face of forward end 92 is in direct contact with the medication contents 74 of cartridge 25.

Body 90 between ends 92 and 94 has a generally cylindrical periphery other than for three radially projecting sealing ribs 98. Each sealing rib 98 extends around the entire circumference of body 90 and is oriented transverse to the axial direction. Each rib 98 includes a radiused sealing surface at its outer radial extent. Of the three rib radiused sealing surfaces, the forward rib sealing surface is 100a, the rearward rib sealing surface is 100c, and the middle rib sealing surface is 100b. As is conventional, ribs 98 are sized and shaped such that sealing surfaces 100a-c press against, in slideable fluid-tight sealing engagement with, the barrel surface 70. The portion of body 90 axially between the ribs 98 does not contact the barrel surface 70.

The sealing ribs 98 are shown as three in number and in axially spaced relationship along the body length, resulting in three different sealing rings for the plunger that provide three axially spaced, peripheral surface regions 100a-c in fluid tight engagement with the barrel surface 70. The number of ribs 98 and resulting surfaces like surfaces 100a-c may be selected by one of skill in the art to provide suitable sealing characteristics in view of the overall design of the plunger. Furthermore, the closer the placement of a sealing ring to the forward face of the plunger, the better the detection of the actual location of the forward face of the plunger which is in contact with the medication. As a result, different numbers of such ribs and sealing surfaces, such as two, or as few as one, or more than three, can be provided, and sensing system 20 may find beneficial application with each of such plunger designs.

Light source 30 typically is positioned to be as a close as possible in the axial direction to the rearward edge 65 of barrel wall 61 at cartridge rearward end 57, and so as to have its generated light be directed in the axial direction through edge 65. The generated light from light source 30 is centered on the middle of the radial thickness of barrel wall edge 65. In alternate embodiments, the light source could be positioned removed from the rearward edge 65 but still configured to provide its light thereto. For example, such as when positioning a light source closer to a power or control source located axially spaced far from the container, and as a result substantially farther from the rear edge, that light source could direct its light into a fiber optic, light pipe or wave guide that in turn directs the light it transmits to the barrel wall rearward edge 65. Such interposed fiber optic, light pipe or wave guide, as well as the light source, alternatively may be so provided within a retainer of the cartridge.

Figure 4:
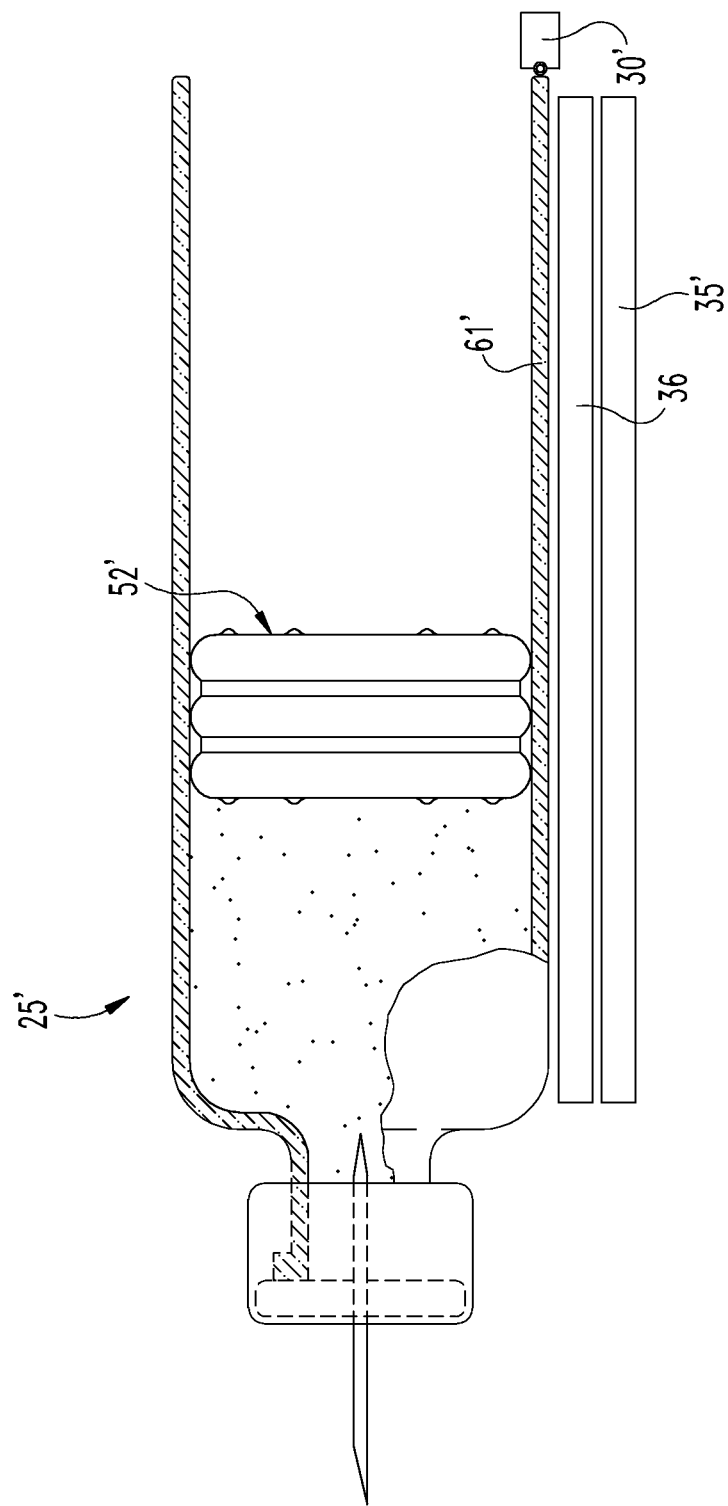
FIG. 4 is a diagrammatic view similar to FIG. 2 but showing an alternate sensing system of the present invention which employs a filtering element.

Light detector 35 is preferably positioned to be as close as possible in the radial direction to the outer periphery of barrel wall 61. In an alternate embodiment shown in FIG. 4 in which like parts are identified with a prime notation, and while light detector 35' is still otherwise positioned as close as possible to barrel wall 61', a light filtering element 36 is interposed between light detector 35' and barrel wall 61'.

Light filtering element 36 has a micro-louver foil to restrict the path of light therethrough such that a wider light beam reflecting off the plunger 52' is channeled into a straight path beam in a single direction by deleting non-perpendicular path of light, specifically the radial direction relative to the cartridge 25'. This filtering serves to enhance contrast for the light detector 35'. An alternative solution can be any type of lens or array of lenses that transform the spreading light reflected off the plunger into a more shaped and focused light beam oriented toward the light detector. For example, collimator lenses can be used.

Figure 3:
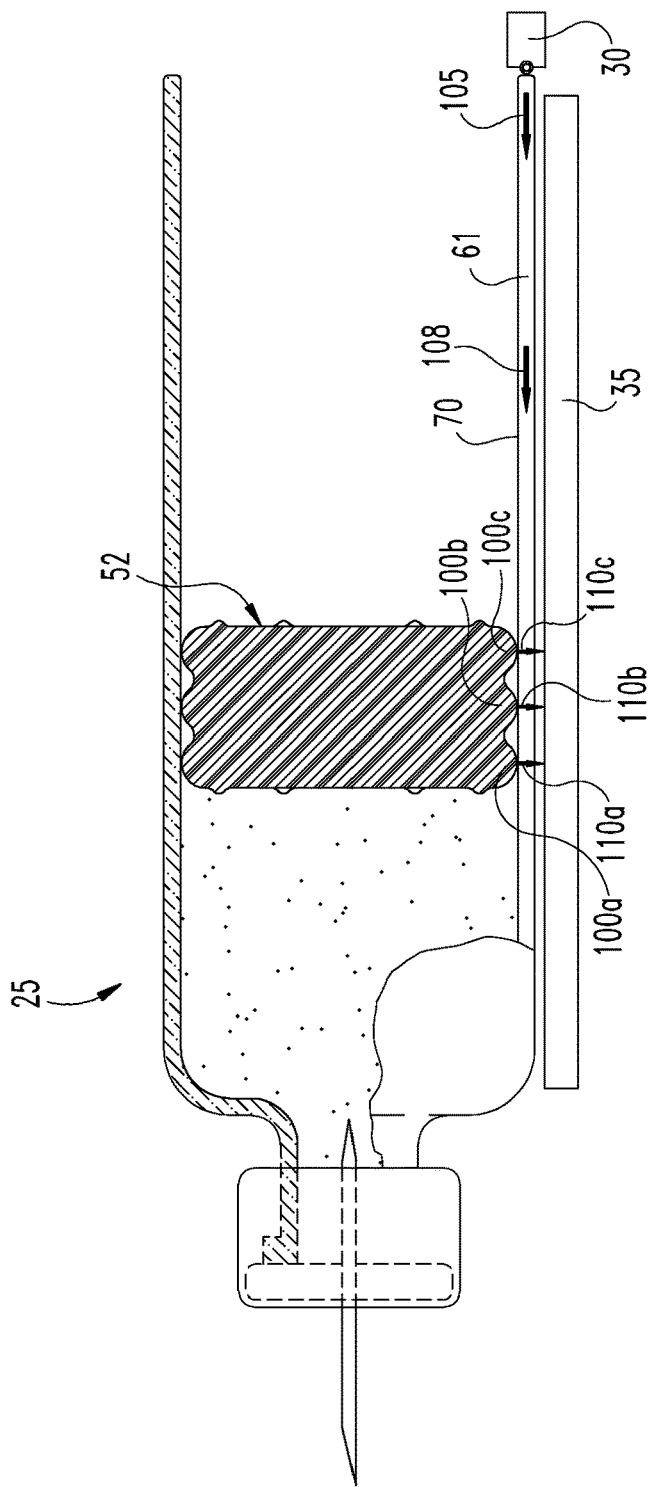
FIG. 3 is a diagrammatic view of the components and cartridge of FIG. 2 wherein light paths are illustrated.

The structure of sensing system 20 will be further understood in view of a description of one way in which it can be operated with additional reference to light paths shown in FIG. 3. When details as to the axial position within cartridge barrel section 60 of one or more of the sealing portions 100a-c of plunger 52 is required, the sensing system 20 is activated. Light source 30 emits a narrow beam of light at 105 in the axial direction into barrel wall 61, which light travels generally internal to wall 61 in the axial direction at 108 due to the axially extending barrel wall 61 acting as a waveguide. The light moving axially in the barrel wall 61 will reflect off so as to illuminate the sealing portions 100a-c of plunger 52 as indicated at 110a, 110b and 110c. These light beams 110a-c, as well as other light from light source 30 passing axially within barrel wall 61 which is reflected radially outward, is sensed by light detector 35 along the detector length or path. The reflected light 110a-c has a higher intensity than the intensity of any light from light source 30 reflecting outward elsewhere along the barrel length, with the intensity tending to decrease from 110c to 110b to 110a due to their distances from the light source 30. The light detector 35 generates electrical signals corresponding to the light intensity levels sensed at various points along its length, which electrical signals are sent via connection 48 to controller 40.

Controller 40 can then process the reflected light data so received from light detector 35 into information related to plunger position or condition that can be stored internally within controller 40, such as for further use, and/or transmitted. The transmitted info could be to, for example, a display associated with cartridge use visible to a user, or a computer network tracking use information. Such transmission means associated with controller 40 are not shown in FIG. 1 but are conventional and may be of a hardwired or wireless variety.

The controller 40 is programmed to determine the positions of sealing portions 100a-c in view of the peaks in the sensed light data along the detector length. For example, the controller 40 may first operate the sensing system a number of times, such as ten, for each occasion the plunger position is desired, resulting in ten values of sensed light data at each pixel, or point of sensing, along the detector length. For each pixel, the ten values are then averaged, and the averaged pixel values are plotted along the detector length to which they correspond. The resulting plot includes three notable upward oscillations, each one corresponding to a different one of sealing portions 100a-c.

The controller then analyzes these oscillations. In one basic system, the controller searches for the pixel with the highest or maximum amplitude within each oscillation, and the axial position of that pixel along the detector length is deemed by the controller to be that of the applicable plunger sealing portion.

Refinements to this basic system may also be used by the controller. In one refinement, a polynomial curve fitting or least squares fitting implementation is used in which a polynomial function is used to approximate the peak region of each oscillation. A region is defined around the detected maximum pixel position of the basic system. In this region the polynomial fitting is calculated obtaining the polynomial coefficients. The polynomial is then evaluated oversampling the pixel, and the refined maximum position is calculated and deemed to be that of the applicable plunger sealing portion. Suitable values for the polynomial fitting area $5^{th}$ degree polynomial, with a fit region of forty pixels on each side of the maximum position, with an oversampling of 100.

In an alternate refinement, a center of area calculation is used for each oscillation. Around each of the detected maximum pixel positions of the basic system, or possibly around the maximum pixel positions as previously refined by the polynomial curve fitting refinement, a region is defined. A suitable region is forty pixels on each side of such maximum position. In this region, the maximum position is calculated with the formula:

$$CentroidMaxPosition = \frac{\sum_{i=1}^{N}(Xi*Yi)}{\sum_{i=1}^{N} Yi}$$

The calculated maximum position value is deemed to be that of the applicable plunger sealing portion.

In an alternate refinement, the position of the whole plunger can be calculated as the position of the maximum value of a cross-correlation function between the output of the sensor and a pre-defined waveform stored in the controller.

Still further, the controller may be programmed to blind portions of detector sensed data associated with reflection at the barrel neck which may otherwise cause the controller to provide an improper readout The information that can be determined by controller 40 may be the quantity of medication 74 forced from cartridge 25 during an injection as calculated based on a change of the axial position of sealing region 100a within barrel section 60 experienced during that injection. Provided other cartridge or history details are known to controller 40, the position of the plunger also may be used to determine the total medication delivered from the cartridge 25 or the total medication remaining in the cartridge 25.

Still further, the controller could also use a reflection at the barrel neck sensed by the detector, which reflection otherwise might have been blinded data as described above, to determine medication remaining in the cartridge. For example, the controller may use the barrel neck reflection sensed by the detector as a reference point, permitting the controller to determine the quantity of medication remaining in the cartridge by comparing the location of the plunger to this reference point. If the controller is to so use the barrel neck reflection, a manufacturing change to the cartridge barrel neck at the point associated with the plunger bottoming out in the cartridge barrel may be provided to more precisely determine such reference point. Such manufacturing change, which heightens the reflection at that point, may be a groove or indentation in the barrel wall, or a protuberance thereat.

Information that can be determined by controller 40 also or alternatively may be an amount of compression of plunger 52. The controller 40 may be programmed to determine if the distance sensed between sealing regions 100a and 100c is less than a stored value for such distance between such sealing regions, whether that stored value be what the distance normally is or what it was immediately before an injection. The plunger compression information could be used to determine residual dose to dispense or to monitor when the plunger 52, after an injection using the cartridge 25 has occurred, has returned to its pre-injection state at which point a cartridge user could be informed that there is no residual dose and that the injection is complete.

Figure 5:
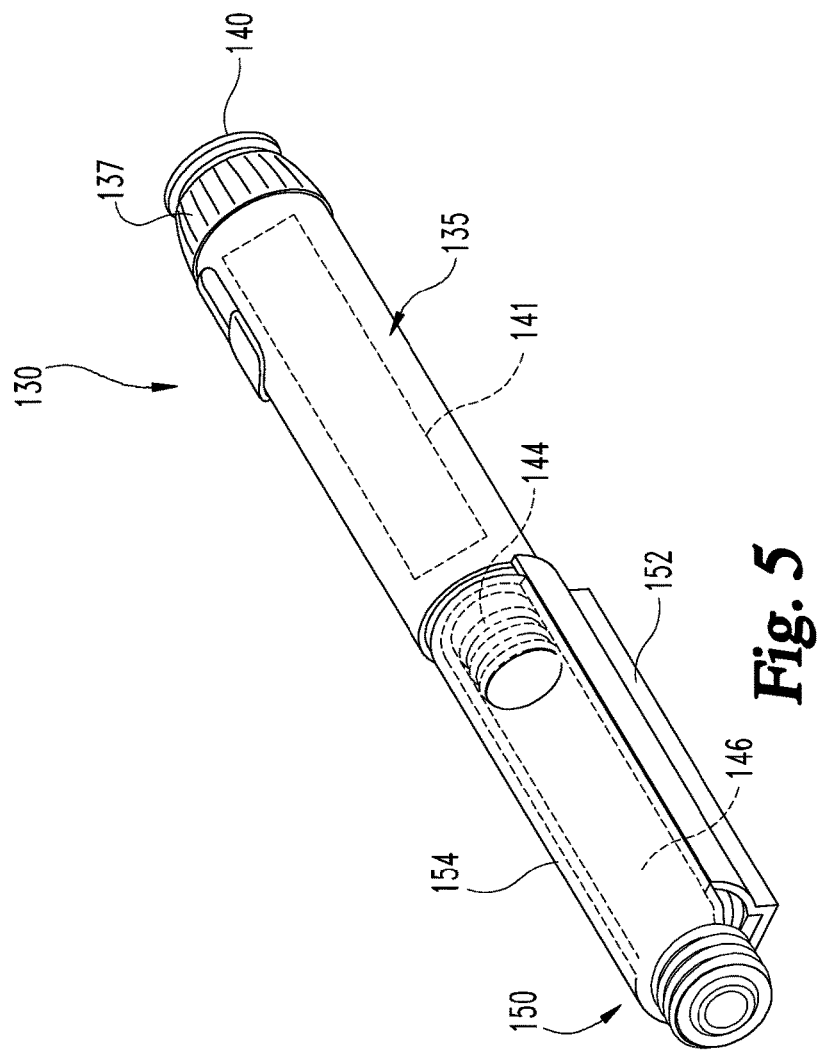
FIG. 5 is a perspective view of an injection pen equipped with a sensing system of the present invention, which pen is shown loaded with a medication cartridge.
Figure 6:
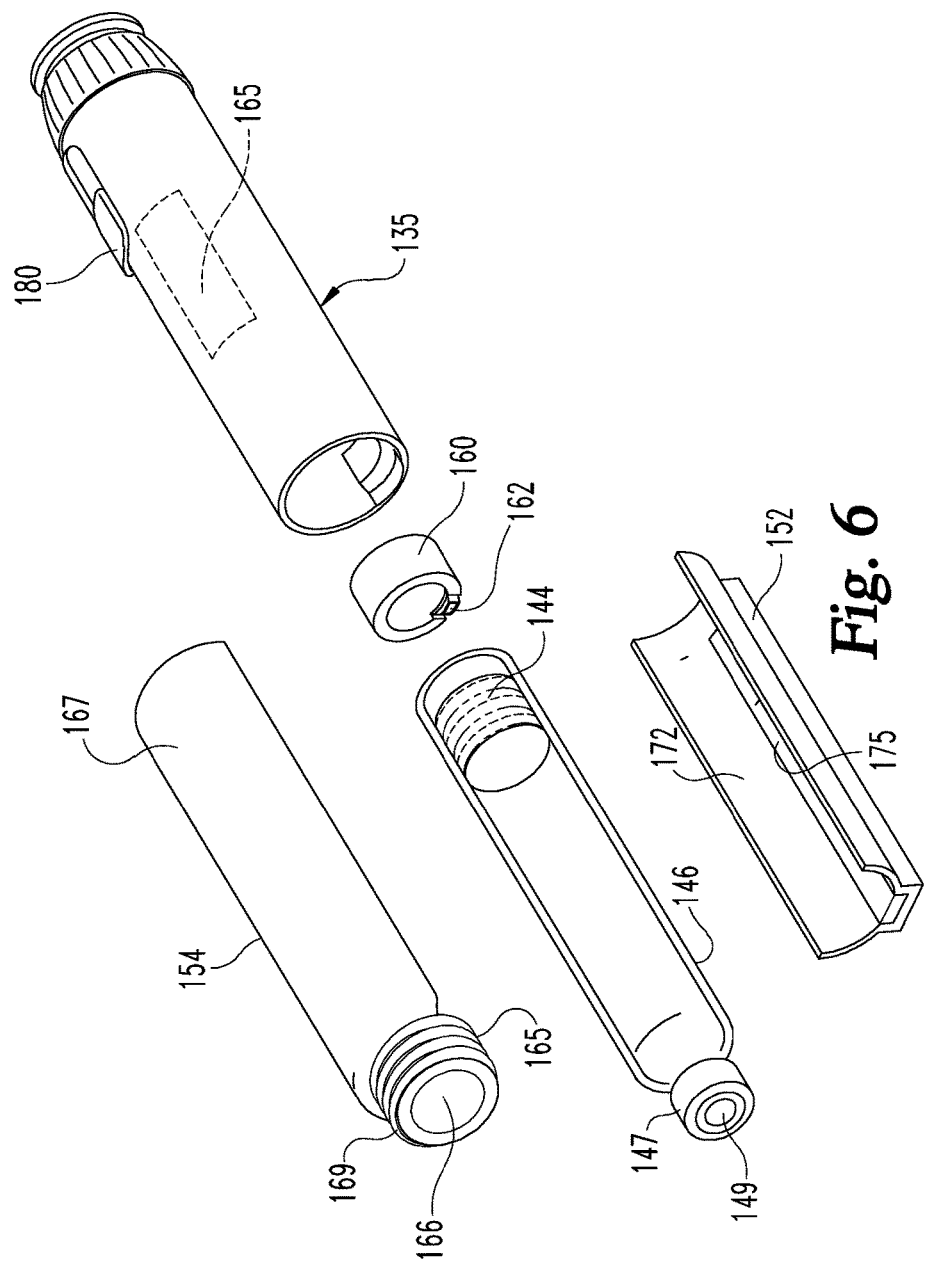
FIG. 6 is an exploded perspective view of select components of FIG. 5.

Referring now to FIGS. 5 and 6, a sensing system similar to system 20 is shown operationally installed in one form of pen-shaped medication injection device generally designated 130. Injection devices of this type are well known, and the description of device 130 is merely illustrative as the sensing system can be adapted for use in variously configured and operating devices in which plunger detection is desired.

Medication injection device 130 is typical of most such devices in including a housing that supports the internal components of the device. The housing is shown as having a rear housing portion 135 which holds a mechanical drive mechanism abstractly indicated at 141. A dose setting collar 137 screws out from housing portion 135 from the position shown in FIG. 5 when turned to set a dose for injection, and application by a user of a plunging force on button 140 carried by the collar 137 moves the button and collar back to their axial positions shown in FIG. 5 which causes drive mechanism 141 to extend its output member from housing portion 135 to advance a plunger 144 forward within cartridge 146.

The sensing system includes a sleeve 160 with a LED 162 which securely mounts within the forward end of rear housing portion 135. The center opening of sleeve 160 allows passage therethrough of the drive mechanism output member. LED 162 serves as the light source of the sensing system and is electrically connected with a power source and sensing system controller within the housing, power source and sensing system controller together are abstractly indicated at 165.

The device housing further includes a two part cartridge retainer or forward housing portion 150 formed of a base section 152 and a top section 154. The retainer 150, when assembled with cartridge 146 therein, is secured to rear housing portion 135 to hold cartridge 146 in an operational position relative to the drive mechanism and the LED 162.

Top section 154 is shown as a transparent cover, having a forward tubular part 165 from which rearwardly extends a curved flange 167 shaped to fit over cartridge 146. Part 165 is sized and shaped for the forward end of cartridge 146 with the crimp seal 147 to insert therein so the cartridge septum 149 is accessible through opening 166. Housing part 165 is externally threaded at 169 to have screwed thereon the hub of a not shown injection needle assembly that when mounted to part 165 provides an injection needle that extends through cartridge septum 149 into communication with the cartridge internal volume for medication delivery to a user of device 130 in a conventional manner.

Base section 152 provides a hollow 172 in which fits cartridge 146. The base of the hollow 172 is formed by an axially extending CMOS array 175 that serves as the light detector of the sensing system. When the forward housing portion 150 is mounted to rear housing portion 135, not shown connectors of the device result in CMOS array 175 being in electrical and data communication with the power source and sensing system controller indicated at 165.

Top section 154 and base section 152 may be configured to connect together in the arranged relationship shown in FIG. 5 to hold the cartridge 146, such as snap fitting together separate parts or via a pivoting together of pinned together parts, before being connected as a unit to rear housing portion 135. Alternatively, either of the top section 154 or base section 152 could be configured to be an extension of the rear housing 135, with the other section being connected thereto, or to the rear housing 135, after cartridge placement. For example, the base section 152 with CMOS array 175 could be fixedly mounted to the rear housing portion 135 so as to extend or project forward therefrom, with cartridge installation occurring by placement of a cartridge 146 onto the base section 152 and then securing the top section 154 to, for example, the rear housing portion 135 over the cartridge 146. Such a design may facilitate the provision of a connection between controller 165 and CMOS array 175.

Due to the presence of the transparent cover that serves as an inspection window that allows a user to see the cartridge, ambient light could affect the measurement of the CMOS array 175. To avoid this two polarized filters 90 degrees rotated themselves could be used, one placed on the inspection window and one stacked on top of the CMOS array, such as together with a micro-louver foil that may be provided on the top of the CMOS array. In this way the cartridge is visible to the user, the array can detect the reflection of the ribs, but external light does not reach the arrays.

Device 130 also includes an electronic display 180, such as a liquid crystal display, shown provided on the side of housing portion 135 and which is electrically connected to controller 165. The display alternatively could be provided elsewhere, such as in housing base section 152. Plunger position information determined by controller 165 using LED 162 and CMOS array 175 could be shown on display 180 to be visible to a user of the device. For example, display 180 could show a numerical indication of how many units were delivered in the last injection use of device 130, or a graphic or alphanumeric notice that an injection is not yet, or is, completed as determined based on whether or not the plunger of the cartridge 146 is compressed.

Figure 7:
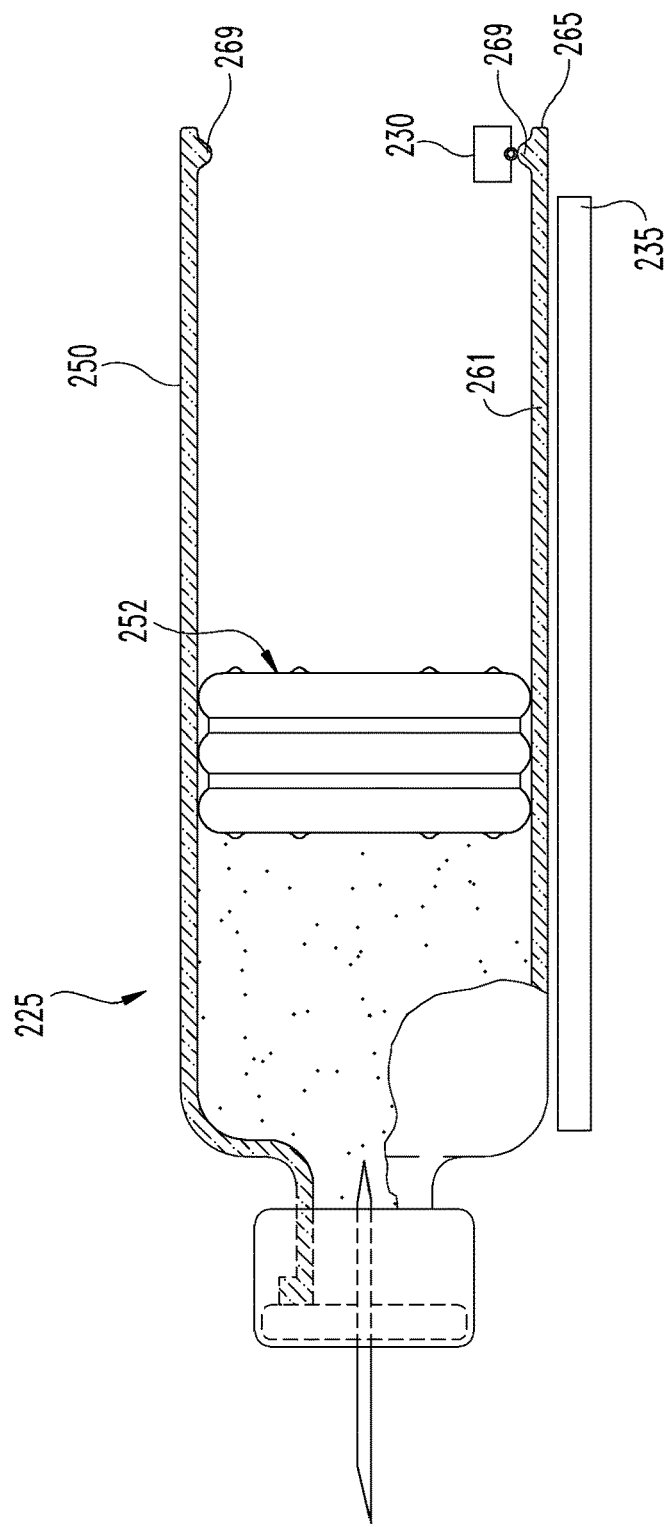
FIG. 7 is diagrammatic view, conceptually similar to FIG. 2, of select components of an alternate sensing system of the present invention adapted for a differently configured cartridge.

Referring to FIG. 7, there is shown another embodiment of the present invention which is adapted to work with a differently configured container known in the art. The sensing system includes a light detector 235 that is the same as the light detector of FIG. 2, and a light source 230 that is similar to light source 30 except for its positioning with respect to the differently configured cartridge 225. Cartridge 225 includes a barrel 250 with a barrel wall 261, and a sealing plunger 252 that are all similar to their corresponding parts in the embodiment of FIG. 2. The barrel 250 differs in that it includes a radial protuberance 269 integrally formed with barrel wall 261. Protuberance 269 is in the form of a circumferential, rounded rib that radially projects from barrel wall 261 into the interior of barrel 250 near the rearward edge 265 of barrel wall 261. Light source 230 is positioned within the barrel 250 and configured to shine light directly incident to the protuberance 269 in a radial direction relative to the axially extending main cartridge wall 261.

Light source 230 is preferably configured, such as by its close placement to protuberance 269 and the narrowness of the light beam it emits, so as not to cast light beams from within the barrel interior directly on any part of the inner surface of barrel 250, except potentially portions in close proximity to protuberance 269 which the controller, by virtue of light detected by the detector 235, can recognize as being so illuminated. A dedicated lens or a group of lenses may be provided to focus the light beam from the light source 230 into protuberance 269.

It has been determined that when light is so directed by light source 230 into protrusion 269, the barrel wall 261 will function as a waveguide so as route that light axially within the barrel wall 261 so as to illuminate the sealing portions of plunger 225 for detection by the sensing system as with the sensing system described with respect to FIG. 2.

Referring to FIG. 8, there is shown still another embodiment of the present invention which is adapted to work with a differently configured container. Cartridge 325 includes a barrel 350 with a barrel wall 361, and a sealing plunger 352 that are all similar to their corresponding parts in the embodiment of FIG. 2. At its rearward end, the barrel wall 351 is integrally formed with a radially outwardly extending protuberance in the form of an orthogonally oriented flange 369. Flange 369 extends beyond the outer periphery of barrel 350 but need not be continuous around the circumference of the barrel. Flange 369 may be utilized to hold the cartridge during the filling process. A larger flange that is finger grippable may be substituted, such as if the flange were the part of a syringe gripped by fingers during manual plunging of the syringe plunger.

The light source 330 directs light inward into the radially outward end of flange 369, resulting in light passing within the length of the flange. The light source may be an annular source of light that rings the cartridge. Detector 335 is a helically configured detector that extends along the length of the barrel through which plunger 352 is movable. Although shown as extending through three full revolutions, a helical pattern used may encompass more or less revolutions, including only a partial revolution if desired. Light source 330 is preferably configured so as not to cast any light beams directly on any part of the outer surface of barrel 350. If some light from light source 330 were allowed to shine directly on the outer surface of barrel 350, it would only be an incidental light that would not compromise the ability of detector 335 to accurately determine the illumination of the plunger sealing portions resulting from the light from source 330 passing through flange 369 in the radial direction relative to the main cartridge barrel 350 and then axially through barrel wall 361 acting as a waveguide. Thus, and except for light from light source 330 moving axially within the barrel wall 361 acting as a waveguide, the configuration of light source 330 does not result in anything more than a minimal or incidental portion of its light reaching a portion of barrel 350 through which the plunger 352 moves while its position is being determined.

Figure 9:
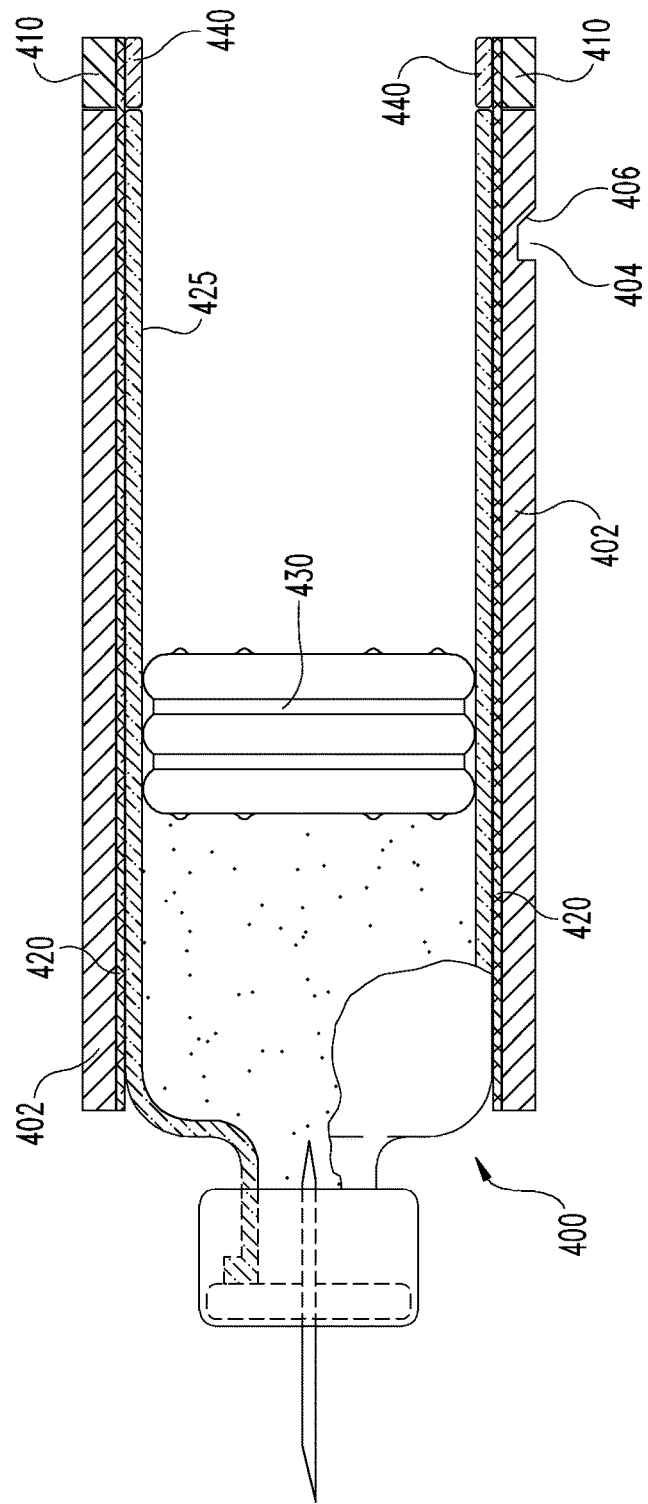
FIG. 9 is diagrammatic view, conceptually similar to FIG. 2, of select components of still another alternate sensing system of the present invention.

While light detectors 35, 35', 175, 235 and 335 are shown as being located only radially of the cartridge barrel, light detectors of the present invention can be positioned to detect light reflected off the sealing plunger by being located in part radially of the cartridge barrel and in other part axially of the cartridge barrel. For example, as shown in FIG. 9, a light detector of the present invention may include a light transmitting portion 402 and a sensing portion 410, with the light transmitting portion 402 being disposed radially outward of the cartridge barrel 425 and the sensing portion 410 being disposed axially rearward of the cartridge barrel 425. The sensing portion 410 is shown in cross section and is provided as an array of CMOS elements or the like arranged in an annular shape near the rearward end of the cartridge 400. The sensing portion 410 is shielded radially from the light source 440 of the sensing system, which light source 440 is an annular array of light emitting diodes aligned with the annular end of the cartridge barrel 425 so as to be concentric with but radially inward of the sensing portion 410.

The light transmitting portion 402 is provided as a sleeve made of a light transmitting material that extends forward from the sensing portion 410 around the cartridge barrel 425. Light transmitting portion 402 serves as a wave guide that routes light in an axial direction within the material of sleeve 402 so as to return to the sensing portion 410 reflected light radially input into light transmitting portion 402. Such reflected light of interest will be the light reflected off the sealing surfaces of plunger 430 after having been first emitted by light source 440 and then traveled through the cartridge barrel 425. A tubular filter element 420 is shown between light transmitting portion 402 and cartridge barrel 425, which filter element 420 selects or allows passage of only strictly radial light. Light transmitting portion 402 may be positioned within, or form in major part, a cartridge retainer of an injection pen.

Light transmitting sleeve 402 is provided with features intended to reflect light that was directed into it radially from the cartridge to move axially through the sleeve wall to reach sensing portion 410. The features are a series of indentations provided in the exterior of sleeve 402 in a helical pattern. One such indentation is shown at 404 but is representative in design of the other indentations in the helical series. The shape and angling of the indentation will be determined based on the properties of the sleeve material, but is shown as having a surface 406 angled at forty-five degrees. Light that is reflected from the cartridge directly radially inward of indentation 404 will pass into the sleeve 402 and impinge surface 406, which surface 406 tends to reflect that light in part directly axially rearward to pass within the wall of sleeve 402 to sensor 410.

The helical pattern of the indentations extends the axial length of sleeve 402 which fits around the portion of the cartridge 400 in which the cartridge plunger 430 may be positioned during use. The helical pattern spans no more than 360 degrees, but the closer to 360 degrees allows for greater resolution provided the annular array of sensor elements within sensing portion 410 is sufficiently dense, and provided the light interference resulting from where the indentations at the start and end of the helical pattern cause the light to reach sensing portion 410 is acceptable The angular orientation of the sensing element 410 to the sleeve 402 is fixed during manufacture, preferably with the sensing element considered to be at the start of the annular sensing portion 410 being angularly aligned with the indentation that is closest in the axial direction to sensing portion 410, and with successive sensing elements in a given angular direction within the annular sensing portion 410 corresponding to successive indentations along the axial direction away from the sensing portion 410. This allows the controller to associate a given pixel with a given position along the sleeve length, and therefore the cartridge length, which allows for positions of the sealing portions of plunger 430 to be determined.

Sleeve 402 may be a cylindrical sleeve and is so shown in the cross-section of FIG. 9 as extending axially forward of indentation 404. As that portion of sleeve 402 that extends forward of the series of indentations does not serve to transmit light back to sensing portion 410, such forward portion may be omitted. In such a modified design, it will be appreciated that the sleeve 402 would appear to be a partial cylindrical sleeve that extends forward from sensing portion 410, but which sleeve has a helically shaped forward edge. Still further, rather than a circular inner and outer periphery, the sleeve 402 may have a polygonal shape, with different surfaces of the polygonal shape being in angular alignment with different ones of the sensing elements of sensing portion 410.

Figure 10:
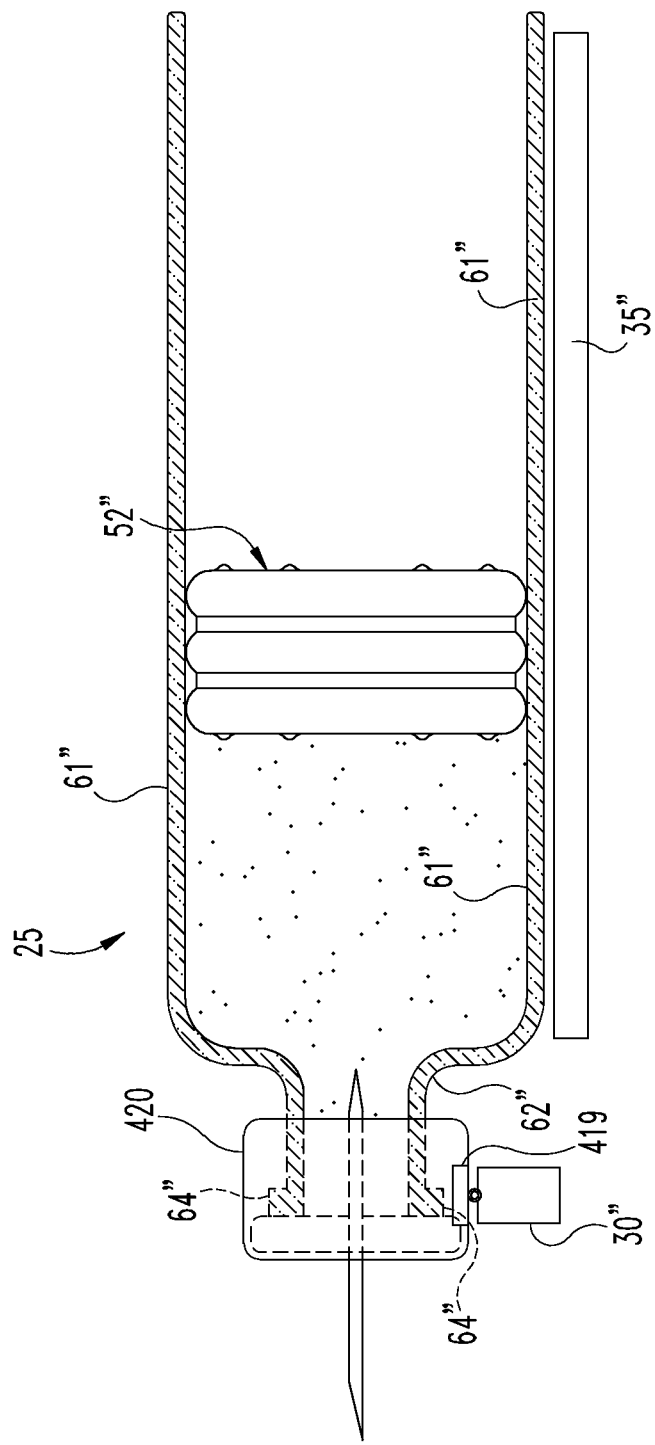
FIG. 10 is diagrammatic view, conceptually similar to FIG. 2, of select components of still another alternate sensing system of the present invention.

Referring to FIG. 10, there is shown still another embodiment of the present invention. In this embodiment, other than a change to the crimp seal and a different positioning of the light source, all the parts are the same as is shown and described with respect to the embodiment of FIG. 2, and are therefore identified here with a double prime notation relative to the parts of FIG. 2. The light source 30" is positioned to direct its light into the collar 64" through an opening or transparency 419 provided in the periphery of a modified crimp seal 420. The collar 64" serves as a radial protuberance integrally formed with barrel wall 61". During use, light from light source 30" passes in a radial direction through the opening 419 of crimp seal 420 and into collar 64", and the light continues through neck section 62" and wall 61" acting as wave guides to illuminate the cartridge wall sealing portions of plunger 52", which illumination is sensed by detector 35" and used as otherwise described above. For proper operation, to have the light from light source 30 pass into opening 419, a system to orient the cartridge relative to the shown sensing system using a single light source 30 is provided to align such window and light source.

Figure 11:
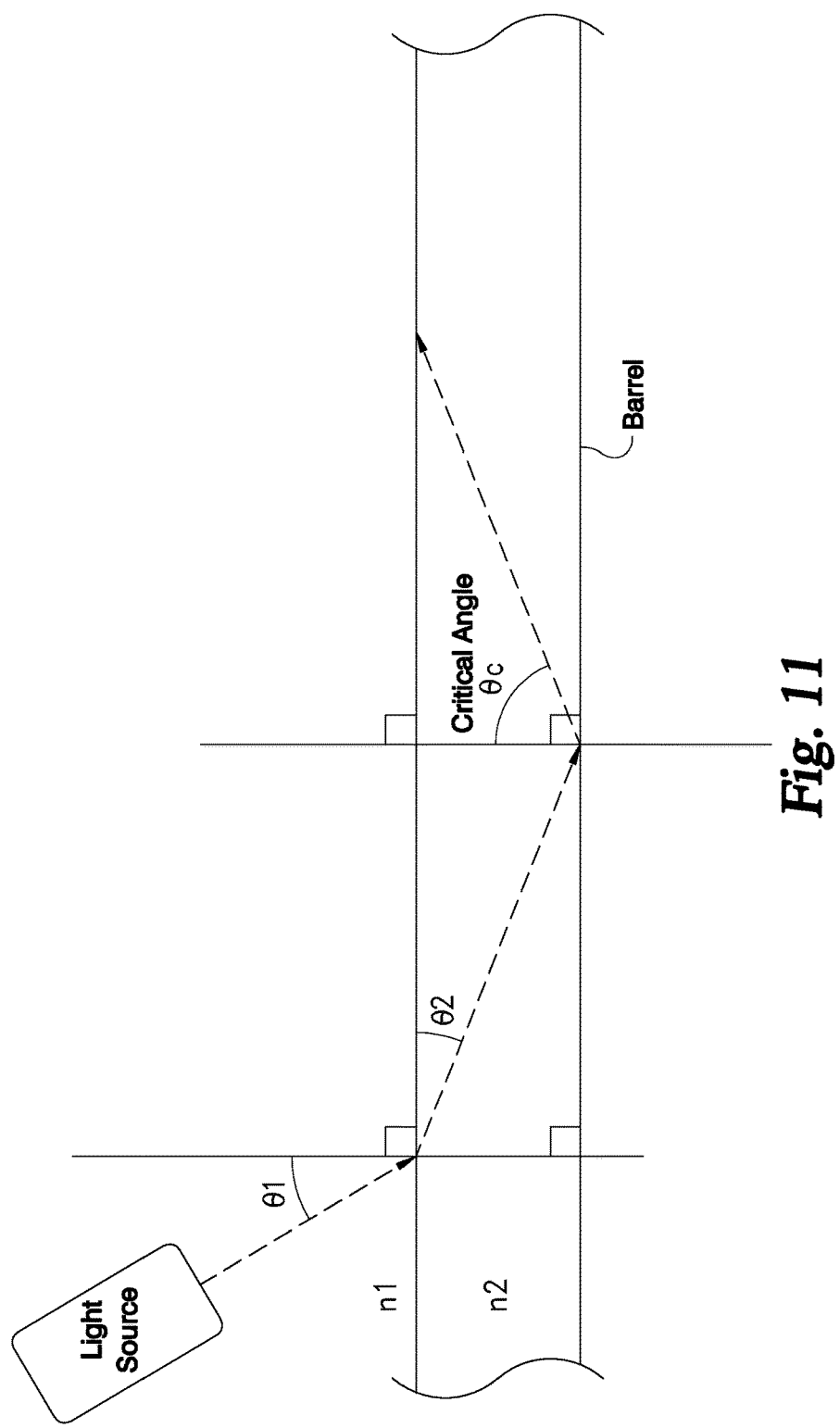
FIG. 11 is a view of a light source emitting light into a barrel wall by directing its light at a defined angle relative to a barrel that is not provided with a surface variation, such as a protuberance, where the light is directed.

While this invention has been shown and described as having preferred designs, the present invention may be modified within the spirit and scope of this disclosure. For example, while the system is shown working with a container barrel having a cylindrical tubular form, it may be used with container barrels having differently shaped tubular forms, such as square or rectangular or oval, and/or with differently shaped plungers. Still further, the system can be used or adapted for use with differently configured cartridges that have features intended to reflect light to move axially through the cartridge barrel wall. While a protuberance is described above as suitable to introduce light properly into the barrel wall for the wall to act as a wave guide, features such as a notch or groove could alternatively be used. Similar to protuberance or flange function, a notch or groove serves as a means to access the container barrel wall to function as a waveguide for the light to travel axially to its target reflective contact surfaces of the plunger. Still further, such protuberance or notch or the like could be placed on the neck section of the cartridge in an alternate embodiment to allow light introduced thereat, such as via a light source situated to shine its light directly into such protuberance, to illuminate the cartridge plunger sealing portions using the barrel wall as a wave guide. Still further, in another not shown embodiment, a light source could be positioned near the neck section of the cartridge and arranged to direct its light beam rearward in an axial direction into the barrel thickness, which light beam, with or without the presence of any protuberance or notch or the like, passes through the interposed portion of the cartridge neck section that transitions to the barrel wall, and into the barrel thickness radially inward of the light detector so that the barrel wall functions as a wave guide. In still another embodiment, and as illustrated in FIG. 11, instead of the light beam being aimed into a barrel wall thickness at either end of the barrel cylindrical wall 61 as described above, or into a protuberance or notch or the like as described above, the light source can be configured to emit light into the barrel wall by directing its light at a defined angle relative to the barrel, including directing its light at an angle relative to the neck section of the barrel. The light should be directed in the plane of the detector element, or in other words in a plane that extends along and through the axis of the detector element and into the barrel. This angle can be determined using the Snell Law to calculate the optimal angle whereby most of the light will be refracted into the barrel wall thickness to then use its waveguide effect for subsequent detection of the reflected light from the plunger by the CMOS detector element. Snell Law is defined as: $n^1 \sin \theta_1 = n_2 \sin \theta_2$, where $n_1$ is the index of refraction for the air, $n_2$ is the index of refraction for the barrel material, $\theta_1$ is the angle of light imparting on the barrel, and $\theta_2$ is the angle of light refracted into the barrel wall thickness. The Critical Waveguide Angle is known for different materials in relation to air including barrel materials and could be designated as $\theta_c$. Referring to FIG. 11, by knowing angle $\theta_c$ and other known values of refractive indices of air and barrel material, one can determine the angle of light $\theta_1$ to be pointed at, for example, the neck section of the barrel relative to the barrel wall. In most optimized embodiments, $\theta_2$ must always be less than $90-\theta_c$ when all angles are in degrees unit. This application is therefore intended to cover any variations, uses or adaptations of the invention using its general principles. Further, this application is intended to cover such departures from the present disclosure as come within known or customary practice in the art to which this invention pertains.

We claim:

1. A medication delivery device comprising:
   a housing including a container retainer;
   a medication container held within the container retainer, the medication container including a barrel and a plunger, the barrel made of a light transmitting material and extending in an axial direction between a forward outlet end and a rearward end, the plunger having at least one peripheral surface region in fluid tight engagement with an interior surface of a wall of the barrel to seal medication in the barrel forward of the plunger;
   an advancing mechanism within said housing operable to advance said plunger within said barrel to dispense medication from the medication container through said forward outlet end;
   a light source mounted within said housing proximate the rearward end of said barrel and configured to emit light directly into a thickness of the barrel wall, the barrel wall configured to serve as a waveguide to guide the light to travel therein in the axial direction, and wherein said light source is a single light emitting diode;
   a light detector mounted within the container retainer and arranged to extend along a length of the barrel to detect reflected light that was emitted by the light source, traveled through the barrel wall serving as the waveguide;
   a controller mounted within the housing in communication with said light detector to determine an axial position of the at least one peripheral surface region within the medication container based on data from said light detector of said detected reflected light.

2. The medication delivery device of claim 1 wherein said light source is configured to direct light into an axial end face of the barrel wall at the rearward end.

3. The medication delivery device of claim 1 further comprising an axially extending light filtering element positioned between said light detector and said barrel wall.

4. The medication delivery device of claim 1 wherein said light source is configured to direct light into a protuberance integrally formed with the barrel wall and projecting therefrom in a radial direction to the thickness of the barrel wall where the light is guided to travel therein in the axial direction.

5. The sensing system of claim 4, wherein the protuberance extends continuously around a circumference of the barrel wall.

6. The sensing system of claim 4, wherein the said light source is configured to direct light into the protuberance that projects radially outward from the barrel wall.

7. The sensing system of claim 6, wherein said protuberance comprises a finger grippable flange of the barrel wall, wherein said flange extends continuously around a circumference of the barrel wall.

8. The medication delivery device of claim 1 further comprising a display in electronic communication with said controller for indicating information determined based on said axial position of said at least one peripheral surface region.

9. The medication delivery device of claim 1 further comprising an actuator accessible externally of the housing and manually operable to control operation of said advancing mechanism.

10. The medication delivery device of claim 1 further comprising a first light polarizing filter and a second light polarizing filter, said first and second light polarizing filters oriented transverse to each other, said first light polarizing filter disposed between said light detector and said container, said second light polarizing filter arranged on said container retainer over said container to restrict ambient light.

11. The medication delivery device of claim 1 wherein said light source emits light into the barrel wall through a fiber optic, light pipe or wave guide disposed therebetween.

12. The medication delivery device of claim 1 wherein said light detector is mounted within the container retainer to detect reflected light that was emitted by the light source, traveled through the barrel wall serving as the waveguide, and then reflected off a neck section of the barrel at the forward outlet end, said detected reflected light associated with said neck section being used by said controller with the determined axial position of the at least one peripheral surface region to calculate an amount of medication remaining in the medication container.

13. The sensing system of claim 1, wherein said light source is positioned to emit light directly at a middle of the thickness of the barrel wall as measured in a radial direction.

14. The sensing system of claim 13, wherein said light source is positioned to be centered on the thickness of the barrel wall.

15. The sensing system of claim 1, wherein said light detector is positioned in close proximity to an outer periphery of said barrel.

16. The sensing system of claim 1, wherein the at least one peripheral surface region comprises first and second peripheral surface regions spaced in the axial direction, and wherein said controller determines a first axial position of the first peripheral surface region and a second axial position of the second peripheral surface region, said controller configured to determine a plunger compression based on the first and second axial positions.

17. The sensing system of claim 1, wherein said light detector is configured to extend around the barrel wall.

18. The sensing system of claim 17, wherein said light detector has a helical configuration.

19. A medication delivery device comprising:
a housing including a container retainer;
a medication container disposed within the container retainer, the medication container including a barrel and a plunger, the barrel comprising a light transmitting material and extending in an axial direction between a forward outlet end and a rearward end, the plunger having at least one peripheral surface region in fluid tight engagement with an interior surface of a wall of the barrel to seal medication in the barrel forward of the plunger;
an advancing mechanism disposed within said housing and operable to advance said plunger within said barrel to dispense medication from the medication container through said forward outlet end;
a light source disposed within said housing and configured to emit light directly into the barrel wall, the barrel wall configured to serve as a waveguide to guide the light to travel therein in the axial direction;
a light detector disposed within the container retainer and configured to detect light that was emitted by the light source and reflected off the at least one peripheral surface region after the light traveled axially through the barrel wall;
a first light polarizing filter and a second light polarizing filter, said first and second light polarizing filters oriented transverse to each other, said first light polarizing filter disposed between said light detector and said container, said second light polarizing filter arranged on said container retainer over said container to restrict ambient light; and
a controller disposed within the housing in communication with said light detector, the controller configured to determine an axial position of the at least one peripheral surface region within the medication container based on data from said light detector of said detected reflected light.

20. The medication delivery device of claim 19, wherein said light source is configured to direct light into an axial end face of the barrel wall at the rearward end.

21. The medication delivery device of claim 19, wherein said light source is configured to direct light into a protuberance integrally formed with the barrel wall and projecting therefrom in an inner radial direction.

22. The medication delivery device of claim 19, wherein said light source is configured to direct light into a protuberance integrally formed with the barrel wall and projecting therefrom in an outer radial direction.

23. A medication delivery device comprising:
a housing including a container retainer;
a medication container held within the container retainer, the medication container including a barrel and a plunger, the barrel made of a light transmitting material and extending in an axial direction between a forward outlet end and a rearward end, the plunger having at least one peripheral surface region in fluid tight engagement with an interior surface of a wall of the barrel to seal medication in the barrel forward of the plunger;
an advancing mechanism within said housing operable to advance said plunger within said barrel to dispense medication from the medication container through said forward outlet end;
a light source disposed within said housing proximate the rearward end of said barrel and configured to emit light centered on a middle of a radial thickness of the barrel wall, the barrel wall configured to serve as a waveguide to guide the light to travel therein in the axial direction;
a light detector disposed within the container retainer and arranged to extend along a length of the barrel, the light detector configured to detect light that was emitted by the light source and reflected off the at least one peripheral surface region after the light traveled axially through the barrel wall; and
a controller disposed within the housing in communication with said light detector, said controller configured to determine an axial position of the at least one peripheral surface region within the medication container based on data from said light detector of said detected reflected light.

24. The medication delivery device of claim 23, wherein said light source is configured to direct light into an axial end face of the barrel wall at the rearward end.

25. The medication delivery device of claim 23, wherein said light source is configured to direct light into a protuberance integrally formed with the barrel wall and projecting therefrom in an inner radial direction.

26. The medication delivery device of claim 23, wherein said light source is configured to direct light into a protuberance integrally formed with the barrel wall and projecting therefrom in an outer radial direction.

* * * * *

UNITED STATES PATENT AND TRADEMARK OFFICE
CERTIFICATE OF CORRECTION

Page 1 of 2

PATENT NO. : 10,384,014 B2
APPLICATION NO. : 15/505699
DATED : August 20, 2019
INVENTOR(S) : Christian Fabio Forlani, Rossano Claudio Massari and Mehran Mojarrad It is certified that error appears in the above-identified patent and that said Letters Patent is hereby corrected as shown below:

In the Claims

Column 14, In Claim 1, Lines 43-44: delete "traveled through the barrel wall serving as the waveguide," and insert -- traveled through the barrel wall serving as the waveguide, and then reflected off the at least one peripheral surface region; and --, therefor.

Column 14, In Claim 5, Line 62: delete "sensing system" and insert -- medication delivery device --, therefor.

Column 14, In Claim 6, Line 65: delete "sensing system" and insert -- medication delivery device --, therefor.

Column 15, In Claim 7, Line 1: delete "sensing system" and insert -- medication delivery device --, therefor.

Column 15, In Claim 13, Line 34: delete "sensing system" and insert -- medication delivery device --, therefor.

Column 15, In Claim 14, Line 37: delete "sensing system" and insert -- medication delivery device --, therefor.

Column 15, In Claim 15, Line 40: delete "sensing system" and insert -- medication delivery device --, therefor.

Column 15, In Claim 16, Line 43: delete "sensing system" and insert -- medication delivery device --, therefor.

Column 15, In Claim 17, Line 51: delete "sensing system" and insert -- medication delivery device --, therefor.

Signed and Sealed this
Twenty-ninth Day of October, 2019

Andrei Iancu
*Director of the United States Patent and Trademark Office*

Column 15, In Claim 18, Line 53: delete "sensing system" and insert -- medication delivery device --, therefor.